United States Patent
Matsuzaki et al.

[11] Patent Number: 5,601,999
[45] Date of Patent: Feb. 11, 1997

[54] ANTITUMOR POLYSACCHARIDE-GLYCAN COMPLEXES

[75] Inventors: Takeshi Matsuzaki; Masato Nagaoka; Koji Nomoto; Shusuke Hashimoto; Teruo Yokokura, all of Tokyo, Japan

[73] Assignee: Kabushiki Kaisha Yakult Honsha, Tokyo, Japan

[21] Appl. No.: 299,414

[22] Filed: Sep. 1, 1994

[30] Foreign Application Priority Data

Sep. 16, 1993 [JP] Japan ................................. 5-252179

[51] Int. Cl.$^6$ ............................. C12P 19/00; C12P 19/04
[52] U.S. Cl. ...................... 435/72; 435/101; 435/244; 435/252.1; 435/252.9; 435/253.4; 536/1.11; 536/4.1; 536/123.1; 514/23; 514/54
[58] Field of Search ........................ 514/23, 54; 435/244, 435/252.1, 252.9, 253.4, 822, 824, 101, 72; 536/1.11, 4.1, 123.1

[56] References Cited

PUBLICATIONS

Patent Abstracts of Japan, vol. 12, No. 479, (C–552) (3326), Dec. 14, 1988, JP–A–63 196 521, Aug. 15, 1988.
Chemical Abstracts, vol. 114, No. 25, Jun. 24, 1991, AN–240 122g.

*Primary Examiner*—James O. Wilson
*Attorney, Agent, or Firm*—Oblon, Spivak, McClelland, Maier & Neustadt, P.C.

[57] ABSTRACT

An antitumor agent is provided by including, as an active ingredient, a polysaccharide-glycan complex obtained by treating a Gram-positive bacteria such as lactic acid bacteria and Bifidobacterium strains with a cell wall lytic enzyme produced by a bacterium belonging to the genus Achromobacter.

The polysaccharide-glycan complex has no toxicity and causes no side effect. Being water-soluble, it is easily formulated into any arbitrary dose form, such as an injectable solution. It can easily be prepared from an easily available starting material.

8 Claims, 1 Drawing Sheet

→ : LINKAGE ATTACKED BY ACHROMOPEPTIDASE
GN : N-ACETYLGLUCOSAMINE
Mur : N-ACETYLMURAMIC ACID
PS : POLYSACCHARIDE

ANTITUMOR POLYSACCHARIDE-GLYCAN COMPLEXES

BACKGROUND OF THE INVENTION

Discussion of the Prior Art

This invention relates to an antitumor agent.

Conventional antitumor agents are divided into chemotherapeutic agents which directly act on a tumor and immunopotentiators which potentiate immunity to bring about an antitumor effect.

Known immunopotentiators include muramyl dipeptide or a polysaccharide constituting microbial cells of tubercle bacillus, hemolytic streptococcus, etc., and the cell wall of these bacteria. However, none of them have achieved sufficient immunopotentiating activity when used alone.

An object of the present invention is to provide a novel antitumor agent which has excellent antitumor activity based on immunopotentiation with reduced side effects and which can be prepared starting with a highly safe bacterium used in food production.

SUMMARY OF THE INVENTION

The present inventors have conducted extensive investigations into the antitumor activities of components constituting the cell walls of a number of bacteria. As a result, they have succeeded in providing an antitumor agent comprising, as an active ingredient, a polysaccharide-glycan complex obtained by treating a Gram-positive bacterium with a cell wall lytic enzyme produced by a bacterium belonging to the genus Achromobacter.

The polysaccharide-glycan complex, the active ingredient of the antitumor agent of the present invention, has no toxicity and causes no side effects. Being water-soluble, it is easily formulated into any arbitrary dose form, such as an injectable solution. Further, it can easily be prepared from a readily available starting material, i.e., microbial cells of lactic acid bacteria or Bifidobacterium strains generally used in food production. Taking advantage of these characteristics, the antitumor agent according to the present invention can be administered through various routes to exhibit high curing effects on tumor cells.

DETAILED DESCRIPTION OF THE INVENTION

Figure 1:
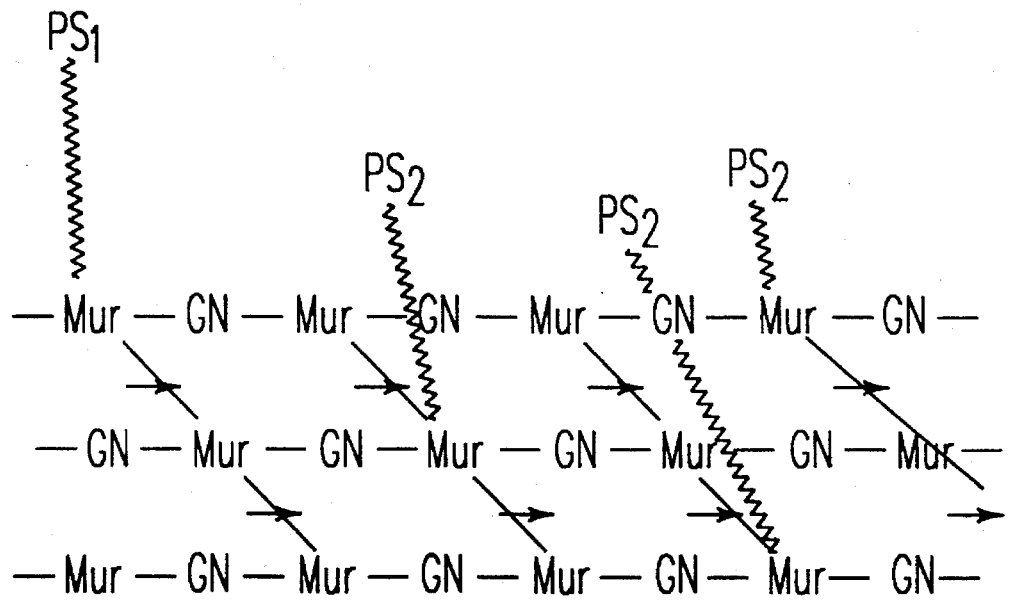
FIG. 1 shows a crossliked network structure of a cell wall.
Figure 2:
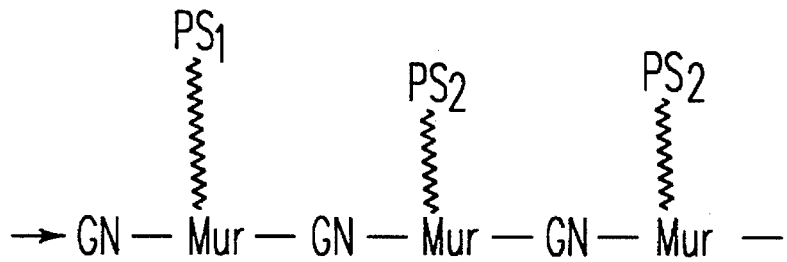
FIG. 2 shows a polysaccharide-glycan complex obtained by hydrolysis of the crosslinking by cell wall lytic enzyme.

The invention will be further explained below.

The cell wall lytic enzyme produced by a bacterium belonging to the genus Achromobacter includes "Achromopeptidase (TBL-1)" sold by Wako Pure Chemical Co., Ltd. The Achromopeptidase (TBL-1) is derived from *Achromobacter lyticus* M497-1.

The cell walls of Gram-positive bacteria, such as lactic acid bacteria and Bifidobacterium strains, are composed of a network structure in which basic sugar chains of N-acetylglucosamine and N-acetylmuramic acid are crosslinked through peptide chains with branches of polysaccharide chains from the residue of the N-acetylmuramic acid. On being treated with Acromopeptidase, the peptide linkages are hydrolyzed to destroy the crosslinkings, leaving the basic sugar chains with the polysaccharide side chains. The unreacted cell walls, low molecular weight compounds, and other impurities are removed by any arbitrary purification means to recover a polysaccharide-glycan complex useful as an antitumor agent.

The Gram-positive bacteria which can be used as a starting material preferably include those utilized in food production, such as various lactic acid bacteria and Bifidobacterium. Suitable examples of lactic acid bacteria are those belonging to the genus Streptococcus, e.g., *S. faecalis, S. faecium, S. thermophilus, S. lactis,* and *S. cremoris,* and those belonging to the genus Lactobacillus, e.g., *L. lactis, L. bulgaricus, L. herbetics, L. acidophilus, L. salibarius, L. casei,* and *L. fermentum.* Suitable examples of the genus Bifidobacterium are *B. longum, B. bifidum, B. breve, B. infantis, B. adolescentis,* and *B. thermophilum.*

The starting microbial cells may be those collected by culture using an arbitrary medium. No special culture is required.

An illustrative example for the preparation of the polysaccharide-glycan complex is shown below.

Heat dead cells (1.5 g) of a lactic acid bacterium was suspended in 150 ml of a 10 mM tris-HCl buffer (pH=8.0), and 100,000 units of Achromopeptidase (TBL-1) were added thereto, followed by incubation at 37° C. for 48 hours. The system was centrifuged at 10,000 rpm for 60 minutes. To the supernatant liquor were added 10 mg of deoxyribonuclease and 10 mg of ribonuclease. After incubation at 37° C. overnight, the system was concentrated by means of an evaporator. The concentrate was dialyzed against distilled water at 4° C. for 24 hours, and the dialysate was lyophilized to obtain a polysaccharide-glycan complex. The polysaccharide portion of the complex had a molecular weight of about 100,000 as measured by gel-permeation chromatography. The complex had such a structure that the polysaccharide portion was bonded to the polymer of muramic acid and glucosamine constituting the cell walls.

The resulting polysaccharide-glycan complex can be used as such or, if desired, after further purification, as an active ingredient of the antitumor agent according to the present invention. The polysaccharide-glycan complex is a water-soluble and stable substance. That is, the lyophilized powder does not undergo reduction in activity even when preserved at room temperature for more than a year. A solution of the powder in physiological saline suffers from no reduction in activity during cryopreservation at −20° C. for 6 months or longer, and the activity is not weakened even if freezing and thawing are repeated three times. Further, heating of the physiological saline solution at 100° C. for 10 minutes results in no activity reduction.

Therefore, the polysaccharide-glycan complex can be formulated by an arbitrary method into injectable solutions, tablets, powders, or other dose forms of antitumor preparations for intravenous injection or oral administration.

A standard dose of the antitumor agent of the present invention is from about 0.8 to 80 mg/kg-body in terms of the polysaccharide-glycan complex.

No toxicity was observed in the polysaccharide-glycan complex as proved by the following $LD_{50}$ values as determined in 7-week-old male BALB/c mice weighing about 25 g:

$LD_{50}$ =2000 mg/kg or more, per os 800 mg/kg or more, intraveneous 800 mg/kg or more, intraperitoneal

EXAMPLES

Methods of the present invention are illustrated with reference to the following examples, but the invention is not intended to be limited only thereto.

The polysaccharide-glycan complexes used in the Examples were prepared in accordance with the above-mentioned method. The antitumor effect of the polysaccharide-glycan complex was determined as follows.

Six 7-week-old male BALB/c mice per group were used as test animals. Meth A fibrosarcoma cells, the isogenic tumor cells, were subcutaneously transplanted to the left inguinal region. On the 3rd, 6th, 9th, 12th and 15th days from the transplantation, the polysaccharide-glycan complex was intravenously injected. On the 21st day from the transplantation, the tumor was excised and weighed. A percent inhibition on tumor growth was obtained according to the following equation:

Tumor growth inhibition (%) =

$$\left(1 - \frac{\text{average tumor weight of test group}}{\text{average tumor weight of control group}}\right) \times 100$$

Example 1

The antitumor effect of a polysaccharide-glycan complex prepared from *Bifidobacterium breve* YIT 4008 (FERM BP-4538) was examined. The polysaccharide-glycan was administered at a dose of 250 μg or 500 μg/animal/dose.

The results obtained are shown in Table 1 below. It is seen that the tumor growth was significantly inhibited by the administration of the polysaccharide-glycan complex.

TABLE 1

| Group | Total Dose (μg) | Average Tumor Weight (g) | Tumor Growth Inhibition (%) |
|---|---|---|---|
| Control | 0 | 2.53 | — |
| Group 1 | 500 × 5 | 0.25 | 90.0 |
| Group 2 | 250 × 5 | 0.27 | 89.4 |

Example 2

The antitumor effect of a polysaccharide-glycan complex prepared from *Lactobacillus fermentum* YIT 0159 (FERM BP-4748) was examined.

The results obtained are shown in Table 2 below. It is seen that the tumor growth was significantly inhibited by the administration of the polysaccharide-glycan complex.

TABLE 2

| Group | Total Dose (μg) | Average Tumor Weight (g) | Tumor Growth Inhibition (%) |
|---|---|---|---|
| Control | 0 | 2.99 | — |
| Group 1 | 500 × 5 | 0.06 | 98.0 |
| Group 2 | 250 × 5 | 0.07 | 97.7 |

Example 3

The antitumor effects of polysaccharide-glycan complex prepared from *Bifidobacterium bifidum* YIT4007 (FERM BP-791), *Lactobacillus salibarius* YIT0089 (ATCC 11742) and *Streptococcus faecalis* YIT2031 (ATCC 19433) was examined.

The results obtained are shown in Table 3 below.

TABLE 3

| Group | Total Dose (μg) | Average Tumor Weight (g) | Tumor Growth Inhibition (%) |
|---|---|---|---|
| Control (saline) derived from | 0 | 2.07 | — |
| *B. bifidum* YIT4007 | 250 × 5 | 0.23 | 88.7 |
| *L. salibarius* YIT0089 | 250 × 5 | 0.06 | 96.9 |
| *S. faecalis* YIT2031 | 250 × 5 | 0.15 | 92.7 |

What is claimed is:

1. An antitumor agent consisting essentially of a polysaccharide-glycan complex obtained by treating a Gram-positive bacteria selected from the group consisting of Streptococcus, Lactobacillus and Bifidobacterium with an achromopeptidase enzyme produced by a bacterium belonging to the genus Achromobacter.

2. The antitumor agent of claim 1, wherein said Gram-positive bacteria is selected from the group consisting of Streptococcus and Lactobacillus.

3. The antitumor agent of claim 1, wherein the achromopeptidase enzyme is a cell wall lytic enzyme produced by *Achromobacter lyticus* M497-1.

4. The antitumor agent of claim 2, wherein said Gram-positive bacteria is selected from the group consisting of *S. faecalis, S. faecium, S. thermophilus, S. lactis, S. cremoris, L. lactis, L. bulgaricus, L. herbetics, L. acidophilus, L. salibarius, L. casei* and *L. fermentum*.

5. The antitumor agent of claim 4, wherein said Gram-positive bacteria is *L. fermentum*.

6. The antitumor agent of claim 1, wherein said Gram-positive bacteria is selected from the group consisting of Bifidobacterium strain.

7. The antitumor agent of claim 6, wherein said Bifidobacterium strain is selected from the group consisting of *B. longum, B. bifidum, B. breve, B. infantis, B. adolescentis* and *B. thermophilum*.

8. The antitumor agent of claim 7, wherein said Bifidobacterium strain is *B. breve*.

\* \* \* \* \*